United States Patent [19]

Ishida et al.

[11] Patent Number: 5,200,270
[45] Date of Patent: Apr. 6, 1993

[54] CARRIER FOR A BIOLOGICALLY ACTIVE COMPONENT FOR IMMUNOASSAY OR ENZYMATIC REACTION

[75] Inventors: Hiroshi Ishida, Machida; Yuji Higo, Nagoya; Masuo Inoue, Komae, all of Japan

[73] Assignee: Toyo Soda Manufacturing Co., Ltd., Shin-nanyo, Japan

[21] Appl. No.: 762,085

[22] Filed: Sep. 19, 1991

Related U.S. Application Data

[63] Continuation-in-part of Ser. No. 400,872, Aug. 30, 1989, abandoned, which is a continuation of Ser. No. 881,692, Jul. 3, 1986, abandoned.

[30] Foreign Application Priority Data

Feb. 25, 1986 [JP] Japan .................................. 61-38279

[51] Int. Cl.$^5$ .................. B32B 5/16; C12N 11/08; G01N 33/545
[52] U.S. Cl. .................................. 428/403; 427/128; 427/131; 427/203; 427/205; 427/222; 428/407; 435/176; 435/180; 435/181; 436/526; 436/531
[58] Field of Search .................. 428/402, 403, 407; 435/176, 180, 181; 436/526, 531; 210/656; 427/128, 131, 203, 205, 222

[56] References Cited

U.S. PATENT DOCUMENTS

| | | | |
|---|---|---|---|
| 4,061,466 | 12/1977 | Sjohölm et al. | 252/408 |
| 4,177,253 | 12/1979 | Davies et al. | 252/62.52 |
| 4,313,734 | 2/1982 | Leuvering | 436/525 |
| 4,369,226 | 1/1983 | Rembaum | 428/334 |
| 4,452,773 | 6/1984 | Molday | 436/529 |
| 4,454,234 | 6/1984 | Czerlinski | 436/526 |
| 4,628,037 | 12/1986 | Chagnon et al. | 436/526 |
| 4,882,226 | 11/1989 | Schutyser et al. | 428/407 |
| 4,885,207 | 12/1989 | Johnson et al. | 428/403 |

FOREIGN PATENT DOCUMENTS

| | | | |
|---|---|---|---|
| 0007654 | 2/1980 | European Pat. Off. | |
| 0038960 | 11/1981 | European Pat. Off. | |
| 0156537 | 10/1985 | European Pat. Off. | 436/526 |
| 0176638 | 9/1986 | European Pat. Off. | |
| 0079266 | 5/1985 | Japan | 436/526 |

OTHER PUBLICATIONS

Patent Abstracts of Japan, vol. 10 No. 374, Dec. 1986.

*Primary Examiner*—George F. Lesmes
*Assistant Examiner*—Christopher Brown
*Attorney, Agent, or Firm*—Oblon, Spivak, McClelland, Maier & Neustadt

[57] ABSTRACT

A carrier for a biologically active component for immunoassay or enzymatic reaction, which comprises:
a) a thermoplastic resin bead having an average diameter of from 0.05 to 20 mm,
b) from 1 to 25% by weight, based on the bead, of a magnetically responsive powder bonded to the bead, and
c) a polymer coated thereon in a thickness of from 2 to 30 μm, said polymer having a number average molecular weight of from 200 to 10,000 and having functional groups capable of binding, or being activated to bind, the biologically active component.

21 Claims, 5 Drawing Sheets

CARRIER FOR A BIOLOGICALLY ACTIVE COMPONENT FOR IMMUNOASSAY OR ENZYMATIC REACTION

This application is a continuation-in-part of application Ser. No. 07/400,872, filed on Aug. 30, 1989, now abandoned, which is a continuation of 06/881,692, filed Jul. 3, 1986, now abandoned.

The present invention relates to a carrier for a biologically active component for immunoassay or enzymatic reaction, and a process for its preparation. More particularly, the present invention relates to a carrier for a biologically active component for immunoassay wherein a very small amount of a substance in a human body fluid is quantitatively and selectively analyzed by an immunological reaction, or for immobilizing enzymes for the industrial utilization of the enzymes.

The immunoassay is a method for quantitatively analyzing the concentration of antigens or antibodies by taking advantage of the specificity of the reaction between antigens and the corresponding antibodies, which reaction takes place even at very low concentrations of the reactants.

The immunoassay generally includes two methods, i.e. a sandwich method and a competition method. In many cases, the immunological reagents comprise immobilized or fixed antibodies or antigens, and labelled antigens or antibodies. The rate of immunological reaction between antigens and antibodies is, by its nature, extremely high, and the binding constant of an antigen-antibody complex is extremely large at a level of from $10^7$ to $10^{12}$ l/mol. Therefore, the antigens or antibodies should be analyzed quickly and quantitatively even if their concentration is low. However, in the actual analysis, there are problems in the reaction rate and the quantitative analysis because of practical difficulties such as the difficulty in stirring the immobilized antibody or antigen carrier particles during the reaction, the non-uniformity of the surface area of the carrier particles, or the insufficiency of the removal of the labelled antigens or antibodies which do not form antibody-antigen complexes (hereinafter referred to simply as "B/F separation").

It is therefore an object of the present invention to overcome such problems.

The present invention provides a carrier for a biologically active component for immunoassay or enzymatic reaction, which comprises:

a) a thermoplastic resin bead having an average diameter of from 0.05 to 20 mm, b) from 1 to 25% by weight, based on the bead, of a magnetically responsive powder bonded to the bead, and c) a polymer coated thereon in a thickness of from 2 to 30 μm, said polymer having a number average degree of polymerization of from 20 to 5,000 and having functional groups capable of binding, or being activated to bind, the biologically active component.

Further, the present invention provides a process for preparing such a carrier, which comprises depositing a magnetically responsive powder on the surface of the thermoplastic resin bead in an amount of from 1 to 25% by weight, based on the bead, and forming a layer of the polymer (c) on the bead in a thickness of from 2 to 30 μm.

Now, the present invention will be described in detail with reference to the preferred embodiments.

In the accompanying drawings.

Figure 1:
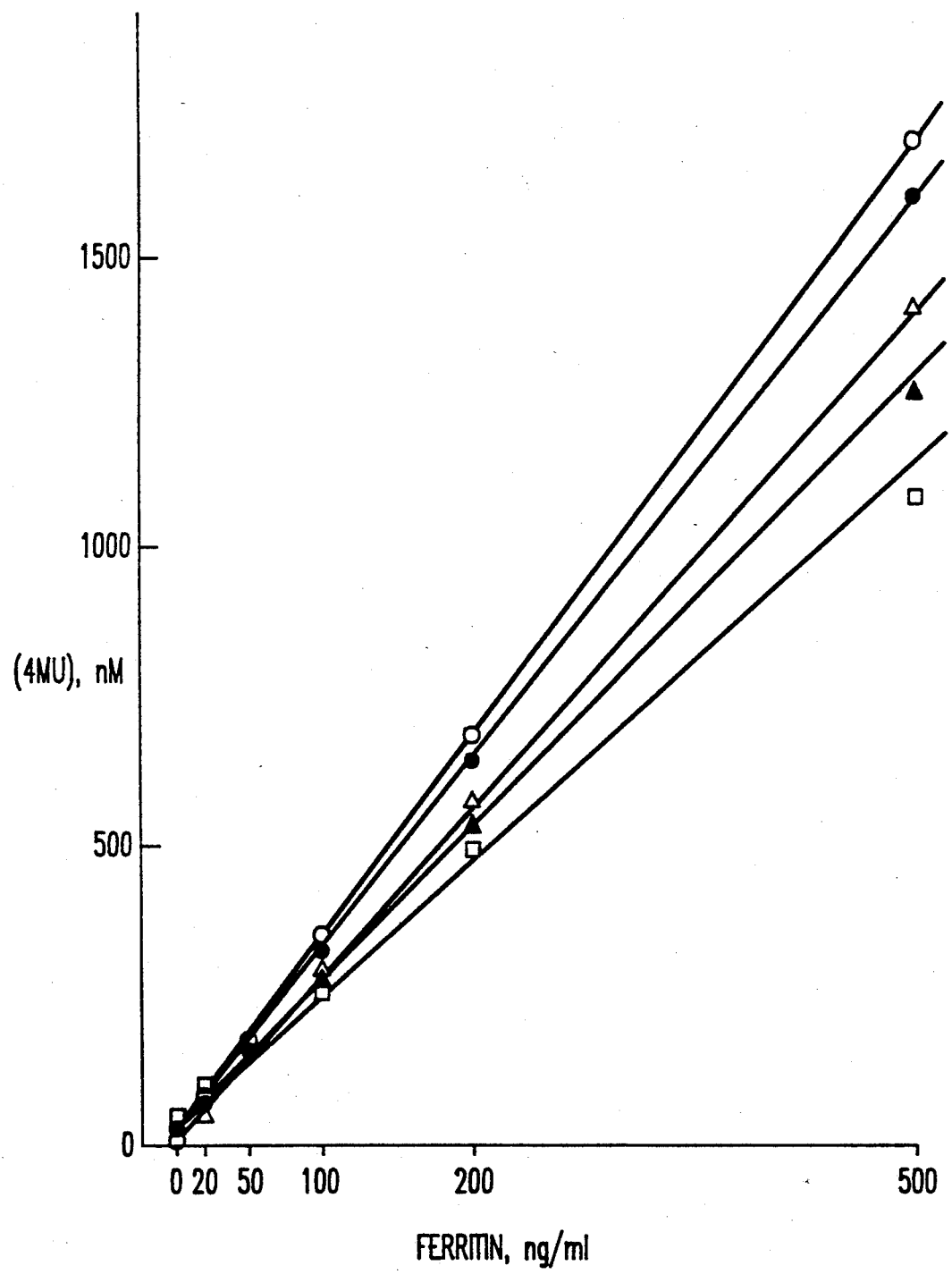
FIG. 1 shows the results of the test for detecting ferritin in Example 8.

The bead constituting the core of the carrier of the present invention is made of a thermoplastic resin which includes a polyolefin such as polyethylene or polypropylene, a vinyl resin such as polyvinyl chloride, polystyrene or polyacrylate, a polyester resin such as polyethylene terephathalate, a polyamide resin such as nylon, a copolymer resin such as an ethylene-vinyl acetate copolymer or a styrene-butadiene copolymer, and a mixture thereof. The thermoplastic resin may further contain fillers. The resin may be pelletized into small sized pellets by a well-known method such as a strand cutting method or an underwater cutting method. It is also possible to use a classified powder of the resin. By using such pellets or powder, beads having a uniform size may be prepared by e.g. extrusion, followed by stretching operation. The beads are preferably substantially spherical. A preferred method for the preparation of such spherical thermoplastic resin beads having a uniform size comprises dispersing a thermoplastic resin having a substantially uniform shape in a medium in which the resin is insoluble, at a temperature lower than the melting point of the resin and then heating the dispersion at a temperature of from the melting point of the resin to a temperature not higher than 30° C. above the melting point.

The average diameter of the thermoplastic resin beads thereby obtained, is determined by the volume of the shaped starting resin particles to be used.

As a dispersant to be used in the method, there may be mentioned a polymer such as polyvinyl alcohol or polyvinyl pyrrolidone, an inorganic fine powder such as alumina or silica, or a surfactant such as a naphthalene sulfonic acid formalin condensation product, sodium oleate, dodecylamine, polyoxyethylenealkyl ether or polyoxyethylenealkylphenol ether. The dispersant is used usually within a range of from 0.001 to 5.0% by weight, preferably from 0.01 to 2.0% by weight, relative to the thermoplastic resin. If the dispersant is outside the above range, coagulation of the resin tends to take place even when the heating is controlled, whereby it is difficult to obtain spherical beads. The heating may be conducted at the melting point of the resin, but in order to facilitate the formation of spherical beads, the temperature may be raised to a temperature not higher than 30° C., preferably not higher than 20° C., above the melting point of the resin.

The medium may be water, an aqueous salt solution, an organic solvent incapable of dissolving the thermoplastic resin, silicon oil, liquid paraffin, a lubricating oil or the like, and it is suitably selected depending upon the melting point of the thermoplastic resin to be treated. The ratio of the medium to the thermoplastic resin may be at any level so long as the thermoplastic resin can be well dispersed in the medium, and the medium is usually in an amount of from 1 to 100% by weight, preferably from 5 to 10% by weight relative to the thermoplastic resin.

The apparatus to be used for the heating and stirring is not required to be of a special type, and may be of a usual type equipped with a jacket or a coil heater and a vane-type stirrer. The dispersed state of the system can be maintained so far as the system is in a flowing state, and can be accomplished by moderate stirring. Thus, smooth spherical beads having a diameter of from 0.05 to 20 mm, preferably from 0.2 to 2.2 mm, can be obtained. The spherical thermoplastic resin beads thus obtained have a uniform surface area and a smooth surface, whereby they can be easily rotated, transferred, dispersed or classified. Therefore, they are useful not only as adsorbents or immobilizing substrates for proteins, but also as supporting substrates for catalysts, magnetic materials or coloring agents.

Then, magnetically responsive powder is deposited on the resin beads. The magnetically responsive powder may be a powder of iron, tri-iron tetroxide, nickel, iron-cobalt, silicon steel or a soft ferrite of the formula $MFe_2O_4$ wherein M is Mn, Zn, Ni, Cd, Cu, Mg, Sr or Ba having an average particle size of from 0.01 to 10 $\mu$m. Such magnetically responsive powder is employed in an amount of from 1 to 25% by weight, preferably from 2 to 15% by weight, based on the thermoplastic resin beads.

The magnetically responsive powder may be deposited on the surface of the thermoplastic resin beads or may be embedded in the beads by heating the thermoplastic resin beads together with the magnetically responsive powder at a temperature within a range of $\pm 50°$ C., preferably $\pm 20°$ C. of the melting point of the thermoplastic resin. The beads having the magnetically responsive powder thus supported thereon will be hereinafter referred to as "magnetic resin beads".

Then, a polymer is further coated on the magnetic resin beads for the purposes of preventing the magnetically responsive powder from falling off and binding a biologically active component such as antigens, antibodies or enzymes.

The polymer coating on the magnetic resin beads may be carried out by a polymerization method wherein a polymerizable monomer dissolved in a solvent or as a bead is, if necessary, together with a usual initiator and cross-linking agent, impregnated to the magnetically responsive powder layer of the magnetic resin beads, followed by heating for polymerization, or a casting method wherein a polymer dissolved in a solvent is impregnated to the magnetically responsive powder layer of the magnetic resin beads, and the evaporating the solvent. The polymer is thereby impregnated into the magnetically responsive powder layer, and therefore the polymer layer thus coated on the magnetic resin beads has substantially the same thickness as the magnetically responsive powder layer, at a level of from 2 to 30 $\mu$m, preferably from 10 to 20 $\mu$m. The solvent to be used for the polymer coating on the magnetic resin beads, has to be a poor solvent or a non-solvent to the thermoplastic resin constituting the magnetic resin beads.

The polymer usually has a number average polymerization degree of from 20 to 5,000, preferably from 100 to 1,000. When a monomer is polymerized together with a cross-linking agent on the surface of the magnetic resin beads to form a polymer coating, the cross-linking agent is adjusted so that the number average polymerization degree between the cross-linkages will be from 1 to 500, preferably from 10 to 50.

The manner for binding a biologically active component such as enzymes, antibodies or antigens, varies depending upon the functional groups of the polymer on the polymer-coated magnetic resin beads thus obtained.

In most cases, the binding or immobilization of the enzymes, antibodies or antigens is conducted in an aqueous solution. Accordingly, the polymer to be coated on the magnetic resin beads should not dissolve or swell in water, and therefore an alcohol-type, ether-type or water-soluble type polymer is not suitable for use. Further, the polymer should not dissolve or swell in a solvent which is used for the activation of the polymer to bind enzymes, antibodies or antigens.

For instance, once hydroxyl groups have been introduced by the modification of the surface layer of the polymer-coated magnetic resin beads, a biologically active component such as enzymes, antibodies or antigens can be immobilized or bound by a conventional method (e.g. N. Hagi et al, Toyo Soda Kenkyu Hokoku 81, 25 (1981)). In some cases, antibodies, antigens or enzymes may be directly reacted to the surface layer for immobilization. Further, a hydrophorbic polymer may be coated, and antibodies, antigens or enzymes may be adsorbed thereon for immobilization.

The polymer to be used for the coating may suitably be selected depending upon the conditions for the immobilization of the biologically active component such as antibodies, antigens or enzymes. Now, the polymer will be described in further detail.

1) Antibodies, antigens or enzymes are chemically bound directly on the surface of the polymer-coated magnetic resin beads. In this case, the magnetic resin beads have to be coated with a polymer having functional groups capable of binding such a biologically active component. For instance, when the beads are coated with a polymer having aldehyde groups, they react with amino groups of the antibodies, antigens or enzymes to form linkages of a Schiff base. The treated beads are then reduced by a reducing agent such as $NaBCNH_3$ to obtain stabilized linkages. As the polymer, there may be employed a polymer of a monomer having the formula RCH=CR'—CHO wherein each of R and R' is a hydrogen atom, an alkyl group, a halogen-substituted alkyl group or a phenyl group, and having a total of from 3 to 10 carbon atoms, preferably from 3 to 6 carbon atoms, such as

2) Only the surface layer of the polymer-coated magnetic resin beads is treated for the immobilization of antibodies, antigens or enzymes. The manner of the treatment varies depending upon the functional groups on the surface layer. The most common functional groups are hydroxyl groups, which may be activated in accordance with a conventional method (e.g. N. Hagi et al, Toyo Soda Kenkyu Hokoku 81, 25 (1981)). Hydroxy groups may be introduced in various manners. However, it is most convenient to employ a method wherein the magnetic resin beads are coated with a polymer having a repeating unit of the formula:

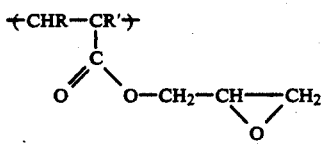

wherein R and R' are as defined above, and then hydrolyzed by sodium hydroxide in a non-aqueous solvent such as methanol or in a non-aqueous solvent mixture. The hydrophilic magnetic resin beads thus obtained, can further be activated in accordance with a conventional method, as described above.

Various groups are conceivable for R and R' in the monomer. However, with a view to the prevention of a non-chemical adsorption to the immobilized layer, the monomer preferably has a total of from 6 to 12 carbon atoms.

When amino groups are to be introduced to the surface layer, the above-mentioned epoxy ring is subjected for a ring opening reaction with a diamine having the formula $NH_2-R''-NH_2$ wherein R" is an alkyl group, a halogen-substituted alkyl group or a phenyl group having a total of from 2 to 12, preferably from 2 to 8 carbon atoms. When the treatment is conducted by using ethylene diamine (R": ethylene), the diamine is added in an amount of more than the stoichiometric amount of the segments of the polymer coated on the magnetic resin beads.

The magnetic resin beads coated with a polymer having epoxy groups may be subjected to partial hydrolysis in accordance with the above-mentioned method. Namely, the partial hydrolysis can be carried out by changing the reaction time or temperature. To the partially hydrolyzed polymer-coated beads, a known silane coupling agent e.g. of the formula:

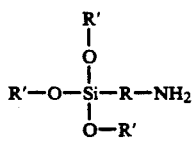

wherein R is an alkyl, aryl or ether group having from 1 to 8 carbon atoms, and R' is an alkyl or aryl group having from 1 to 8 carbon atoms, which is stable in water or in a non-aqueous solution, is reacted. In this case, after the completion of the reaction, the surface layer will have amino groups and hydroxyl groups in the form of

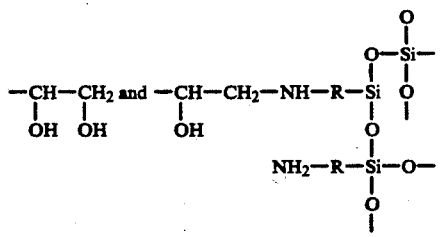

wherein R is as defined above.

3) As other polymers which may be employed for the coating layer of the magnetic resin beads, polymers or copolymers of vinyl chloride, styrene or its derivatives, which are used as the base material for microtiter plates commonly employed in an immunoassay, may be mentioned, although they are not necessarily preferred since they require a plurality of steps for the surface activation. The activation treatment may be conducted as the case requires, in accordance with conventional methods.

Now, the present invention will be described in further detail with reference to Examples. However, it should be understood that the present invention is by no means restricted to these specific Examples.

EXAMPLE 1

Preparation of resin beads 4 kg of ethylene-vinyl acetate copolymer pellets (Ultracene 710, trade name, manufactured by Toyo Soda Manufacturing Co., Ltd., melting point: 75° C.) having an average diameter of 1.4 mm and an average length of 1.5 mm obtained by an under water cutting method, were added to 20 liter of an aqueous solution containing 0.5 wt. % of polyvinyl alcohol (polymerization degree: about 500), and mixed and dispersed by a vane-type stirrer. The dispersion is heated by a coil heater to a temperature of 95° C., and the stirring was continued for one hour. Then, the heating was stopped, and the dispersion was left to cool naturally. After cooling, the resin beads were separated, washed with water and dried. The resin beads thus obtained are spherical with an average diameter of 1.65 mm and had a smooth surface. The yield was 95%.

EXAMPLE 2

Preparation of resin beads 35 g of low density polyethylene pellets (Petrocene 356, trade name, manufactured by Toyo Soda Manufacturing Co., Ltd., melting point: 101° C.) having an average diameter of 2 mm and an average length of 2.5 mm obtained by an under water cutting method, were added and dispersed in 50 ml of an aqueous solution containing 3.5% by weight of polyvinyl alcohol (polymerization degree: about 500). The dispersion was dropwise added to 2 liter of polyethylene glycol heated to 115° C., and after stirring for 15 minutes, left to cool naturally. After cooling, the resin beads were separated, washed with water and dried. The resin beads thus obtained were spherical with an average diameter of 2.5 mm. The yield was about 80%.

EXAMPLE 3

Preparation of resin beads 1 kg of ethylene-vinyl acetate copolymer pellets (Ultracene 710, trade name, manufactured by Toyo Soda Manufacturing Co., Ltd., melting point: 70° C.) having an average diameter of 1.4 mm and an average length of 1.5 mm obtained by an under water cutting method, were added to 5 liter of an aqueous solution containing 6% by weight of Extran MA (manufactured by Merck Co.), and heated and stirred at 95° C. for one hour. After cooling naturally, the resin beads were separated, washed with water and dried. The resin beads thus obtained were spherical with an average diameter of 1.65 mm. The yield was about 95%.

EXAMPLE 4

Preparation of resin beads 100 g of polystyrene pellets (Denka Styrol 9p-2, trade name, manufactured Denki Kagaku Kogyo Kabushiki Kaisha, melting point: 185° C.) having an average diameter of 2.0 mm and a length of 3.0 mm prepared by a strand method, were added to 1 liter of polyethylene glycol having 90 g of ferrite (wet-type ferrite, manufactured by Toyo Soda Manufacturing Co., Ltd., particle size: 0.3 μm) dispersed therein, and the mixture was heated and stirred at 200° C. for 30 minutes. After rapidly cooling with cool water, the resin beads were separated, washed and dried. The resin beads thus obtained were spherical with an average diameter of about 2.6 mm. The yield was 100%.

COMPARATIVE EXAMPLE 1

35 g of the same polyethylene pellets as used in Example 2 were added to 2 liter of polyethylene glycol without being dispersed in polyvinyl alcohol. The dispersion was heated and stirred at 115° C. for 15 minutes, and then left to cool naturally, whereby the resin underwent coagulation.

EXAMPLE 5

300 g of spherical beads of an ethylene-vinyl acetate copolymer (EVA) obtained in Example 1 and 60 g of a soft ferrite of the formula $(Mn,Zn)Fe_2O_4$ having an average particle size of 0.3 μm were introduced into a 2 liter flask, and thoroughly mixed at room temperature by means of a rotary evaporator. The mixture was heated under stirring while measuring the temperature of the beads. When the temperature reached 90° C., the heating was stopped, and the mixture was maintained at that temperature for from 15 to 20 minutes, and then gradually cooled. In the magnetic resin beads thus obtained, the ferrite particles are not firmly bonded, and a part of ferrite particles fell off by abrasion. However, the deposited ferrite particles were not completely removed, and 80% by weight of the ferrite particles were found to be fused in the EVA in a thickness of from 5 to 15 μm by the electron microscopic (SEM) observation of the magnetic resin beads. Further, the spherical degree of the beads was found unchanged from the initial spherical degree.

Then, the magnetic resin beads thus obtained were coated with the following polymers.

(1) A solution mixture comprising 15 g of an acrolein monomer, 0.6 g of tetraethyleneglycol dimethacrylate and 0.2 g of benzoylperoxide (BPO) as an initiator, was impregnated to 100 g of the magnetic resin beads under stirring. Then, the mixture was heated to 60° C. and polymerized for about 3 hours. After the polymerization, the product was washed with ethanol to remove the unreacted monomers. In this operation, about 5% by weight of ferrite particles were removed.

(2) An acetone solution containing 30% by weight of glycidyl methacrylate (GMA) was prepared. BPO was added as an initiator, and the polymerization was conducted at 60° C. for 5 hours. The polymer thus obtained had a number average molecular weight of about 40,000. This polymer solution was diluted with acetone to a concentration of 5% by weight. 30 g of this polyglycidyl methacrylate acetone solution was gradually added to 100 g of the magnetic resin beads under stirring, and acetone was evaporated to conduct the coating of the impregnated polymer. Acetone was further evaporated in vacuum from the polymer-coated magnetic resin beads thus obtained.

Then, the beads thus obtained were treated in the following two methods.

In the first method, the epoxy groups on the surface layer were subjected to a ring opening reaction with a 5 wt. % sodium hydroxide methanol solution to convert the epoxy groups to diols.

In the second method, the epoxy groups on the surface layer were subjected to a ring opening reaction with a 65 wt. % ethylenediamine aqueous solution for 5 hours to introduce amino groups to the surface in the form of

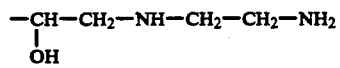

100 g of the GMA-coated magnetic resin beads were introduced into an Erlenmeyer flask, and 200 g of a 65 wt. % 1,6-diaminohexane aqueous solution was added and reacted thereto for 12 hours. After the reaction, the beads were washed with water. Amino groups were introduced to the surface in the form of

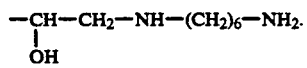

The product had poor wettability with water as compared with the beads aminated with ethylenediamine.

Further, 100 g of the GMA-coated magnetic resin beads were introduced into an Erlenmeyer flask, and 200 g of a 40 wt. % $NH_2-(CH_2)_{12}-NH_2$ ethanol solution was added and reacted thereto for 12 hours under stirring. Amino groups were introduced to the surface in the form of

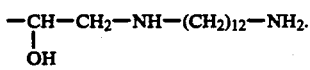

100 g of the GMA-coated magnetic resin beads were subjected to hydrolysis for about 1 hour in 200 ml of a 5 wt. % sodium hydroxide methanol solution. Then, the beads were treated with a 40 wt. % triethoxy-3-aminopropyl silane aqueous solution, whereby magnetic resin beads having amino groups on their surface were obtained.

The amino groups were detected by a ninhydrin method. Further, the amount of the epoxy groups on the surface was determined by treating the GMA-coated magnetic resin beads with a dimethyl amino aqueous solution, washing them with water until the pH became 7, and titrating with hydrochloric acid for neutralization.

(3) To 100 g of the magnetic resin beads, a monomer solution comprising 11 g of a glycidyl methacrylate monomer, 0.2 g of tetraethylene glycol dimethacrylate and 0.1 g of BPO as an initiator, was impregnated at room temperature under stirring. The mixture was stirred at 60° C. for 2 hours to conduct the polymer coating. The product was washed with ethanol, and then subjected to the same activation treatment as in (2).

EXAMPLE 6

Ethylene-vinyl acetate copolymer pellets (Ultracene 625, tradename, manufactured by Toyo Soda Manufacturing Co., Ltd. melting point: 90° C.) were pulverized by a turbomill (T-400 Test Machine, manufactured by Turbo Rogyo Co.). The particle size distribution of the particles were such that particles of from 24 to 34 mesh constituted 37% by weight. Then, 1 kg of such particles were dispersed in 10 liters of a 2 wt. % polyvinyl alcohol aqueous solution at room temperature under stirring. The temperature was gradually raised, and the mixture was stirred at 95° C. for about 2 hours, and then gradually cooled. When the temperature reached a level of from 35° to 40° C., the product was taken out, and the polyvinyl alcohol deposited on the surface was decomposed with sodium hypochlorite and removed. After drying, the product was classified to obtain a fraction of from 24 to 34 mesh, which constituted 70% by weight. By such treatment for spherical beads, the classification efficiency was improved, and the particle size distribution became sharp or narrow.

Then, 300 g of the particles were introduced into a Kjeldahl shaped flask, and 30 g of ferrite was added. The mixture was stirred at room temperature by means of an evaporator, and the ferrite was substantially uniformly deposited on the surface of the particles. Then, the ferrite-deposited particles were heated in an oil bath at 110° C. for 15 minutes, and then cooled, and the particles were taken out. Thus, ferrite was coated on the surface of the particles.

To a 30 wt. % glycidyl methacrylate acetone solution, a 0.5 wt. % benzoyl peroxide was added, and the mixture was polymerized at 60° C. for 8 hours. The polymerization was terminated with a small amount of methanol. This coating polymer had a number average molecular weight of 48,000, and its molecular weight distribution (weight average molecular weight/number average molecular weight) was 2.8. This 30 wt. % polyglycidyl methacrylate acetone solution as the reaction solution was diluted with acetone to a concentration of from 1 to 5% by weight.

330 g of the ferrite-coated particles were introduced into a planetary type stirrer, and 150 g of the 5 wt. % polyglycidyl methacrylate acetone solution was sprayed under stirring in an air stream to form a polymer coating. Then, the polymer-coated magnetic resin beads were introduced into an evaporator, and adequately dried in vacuum under stirring at a temperature of 60° C. The polyglycidyl methacrylate-coated magnetic resin beads were added to 700 g of a 5 wt. % methanol sodium hydroxide solution, and hydrolyzed at room temperature for 8 hours. Then, the beads were adequately washed with water, and then dried. The apparent specific gravity of the beads was from 1.04 to 1.08, and the particle size distribution was the same as immediately after the treatment for spherical beads.

EXAMPLE 7

Polyethylene pellets (Petrocene 356, tradename, manufactured by Toyo Soda Manufacturing Co., Ltd., melting point: 101° C.) was pulverized by the same turbomill as used in Example 6. The particles thus obtained had a particle size distribution such that particles of from 24 to 60 mesh constituted 85% by weight. To 300 g of these particles, 60 g of ferrite (0.3 μm, $(Mn,Zn)Fe_2O_4$) was added, and the mixture was introduced into a 1 liter Kjeldahl shaped flask, and stirred at room temperature by an evaporator to uniformly deposit ferrite on the surface of the polyethylene particles.

Then, the ferrite-deposited particles were gradually heated under stirring to 110° C., maintained at that temperature for 15 minutes and then gradually cooled. 150 g of the magnetic resin beads thus obtained were treated with 80 g of a THF solution of 5 wt. % polystyrene (Denka Styrol 9D-2, tradename, manufactured by Denki Kagaku Kogyo Kabushiki Kaisha) in the same manner as in Example 5 to form a polystyrene coating on the surface of the beads. No substantial peeling off of ferrite from the polystyrene-coated magnetic resin beads was observed. From the observation of the surface of the beads by SEM, it was found that the surface after the ferrite coating was an irregular surface with ferrite deposited thereon without fusion, whereas the surface after the polystyrene coating, was smooth and had a thickness of from 2 to 15 μm in its cross-section.

Separately, 150 g of the magnetic resin beads were treated with 80 g of a THF solution of 5 wt. % polyvinyl chloride (Ryulon paste, tradename, manufactured by Toyo Soda Manufacturing Co., Ltd.) in the same manner as in Example 5 to form a polyvinyl chloride coating on the surface of the beads. No substantial peeling off of ferrite was observed.

EXAMPLE 8

By using the polymer-coated magnetic resin beads (diameter: about 1.6 mm) obtained in Example 5(3), an enzymatic immunoassay of ferritin was conducted by a sandwich method. Namely, five types of magnetic resin beads i.e. (1) those having alcoholic hydroxyl groups formed by saponification on the surface, (2) those having amino groups formed by treatment with ethylenediamine on the surface, (3) those having amino groups formed by treatment with 1,6-diaminohexane on the surface, (4) those having amino groups formed by treatment with 1,12-diaminododecane on its surface and (5) those having amino groups formed by the treatment with triethoxy-3-aminopropylsilane on its surface, were employed.

Binding of antibodies on beads (1) (CDI method):

Magnetic resin beads (2000 beads) having alcoholic hydroxyl groups were adequately dried, and vigorously stirred with 5.0 ml of dry acetone containing 100 mg of N,N'-carbonyl diimidazole (CDI) in a nitrogen atmosphere at room temperature for 30 minutes. The activated magnetic resin beads thus obtained were washed, and 4.0 ml of a basic buffer solution containing 4.0 mg of anti-ferritin monoclonal antibodies, was added thereto for immobilization. Then, non-specific adsorption portions were blocked with bovine serum albumin (BSA) in accordance with a usual method.

Binding of antibodies on beads (2) to (5)
(ethylenediamine method, 1,6-diaminohexane method, 1,12-diaminododecane and silane coupling agent method, respectively)

Magnetic resin beads (2000 beads) having amino groups were treated with a basic buffer solution containing glutaraldehyde at room temperature, and then thoroughly washed to remove excessive glutaraldehyde. Then, 4.0 ml of a basic buffer solution containing 4.0 mg of anti-ferritin monoclonal antibodies, was added thereto for immobilization by the formation of a Schiff base. Then, the Schiff base was reduced by sodium cyanoborohydride to form stable chemical bonds. Then, in the same manner as mentioned above, non-specific adsorption portions were blocked with BSA.

By using another monoclonal antibodies capable of forming a sandwich with the above-mentioned immobilized antibodies, an enzymatic immunoassay was conducted by means of antibodies labelled with an alkaline phosphatase (EC 3.1.3.1) derived from bovine intestinal mucosa. Namely, 12 antibody-bound magnetic resin beads were introduced into separate immunoassay reactors, and 20 microliters of a serum containing 0, 20, 50, 100, 200 or 500 ng/ml of ferritin and 125 microliters of the enzyme-labelled antibody solution were added to the respective reactor, whereupon the antigen-antibody reaction was conducted at 37° C. for 40 minutes. After washing and solid-liquid separation (B/F separation), 100 microliters of a 1 mM 4-methylumbelliferyl monophosphate as the substrate for the alkaline phosphatase was added, and the enzyme-substrate reaction was conducted at pH 10.0 at 37° C. for 10 minutes. Then, 2.9 ml of a quenching solution was added to terminate the reaction. The fluorescence of this solution was measured at an excitation wave length of 360 nm and at an emission wave length of 450 nm. The results are shown in FIG. 1. The abscissa indicates the concentration of ferritin as the antigen, and the ordinate indicates the fluorescence intensity, whereby the concentration of the formed 4-methylumbelliferone (4MU) is presented by nM unit. In FIG. 1, ○: CDI method;   ●: 1,6-diaminohexane method;
△: ethylenediamine method;
▲: silane coupling agent method; and
□: 1,12-diaminododecane method.

EXAMPLE 9

By using the magnetic resin beads (diameter: about 1.6 mm) obtained in Example 5(3), a study was made on the binding of the antibodies. As the magnetic resin beads, the same five types as used in Example 8 were employed, and the respective binding of antibodies was conducted in the same manner, except that instead of the antibodies, $^{125}$I-labelled mouse IgG was used for immobilization as a substitute for the monoclonal antibodies. IgG was employed in an amount of 1, 2, 4 and 8 μg per one magnetic resin bead. The results obtained are shown in Table 1.

TABLE I

| Amount of bound IgG per magnetic resin bead | | | | |
|---|---|---|---|---|
| Amount of IgG added | 1 μg/bead | 2 μg/bead | 4 μg/bead | 8 μg/bead |
| CDI method | 0.82 μg | 1.20 μg | 1.56 μg | 1.82 μg |
| Ethylenediamine method | 0.72 μg | 1.08 μg | 1.42 μg | 1.68 μg |
| 1,6-Diaminohexane method | 0.78 μg | 1.16 μg | 1.54 μg | 1.84 μg |
| 1,12-Diaminododecane method | 0.63 μg | 0.96 μg | 1.28 μg | 1.49 μg |
| Silane coupling method | 0.71 μg | 1.04 μg | 1.42 μg | 1.66 μg |

It is evident from Table 1 that the amount of bound IgG and the antigen-antibody reaction (see FIG. 1) have good correlation to each other. Namely, this is evident from the comparison of the respective immobilization methods at the amount of IgG added being 2 μg/bead with the results of FIG. 1. Further, from the Table, it is seen that each magnetic resin bead is capable of binding only 2 μg of IgG.

EXAMPLE 10

Figure 2:
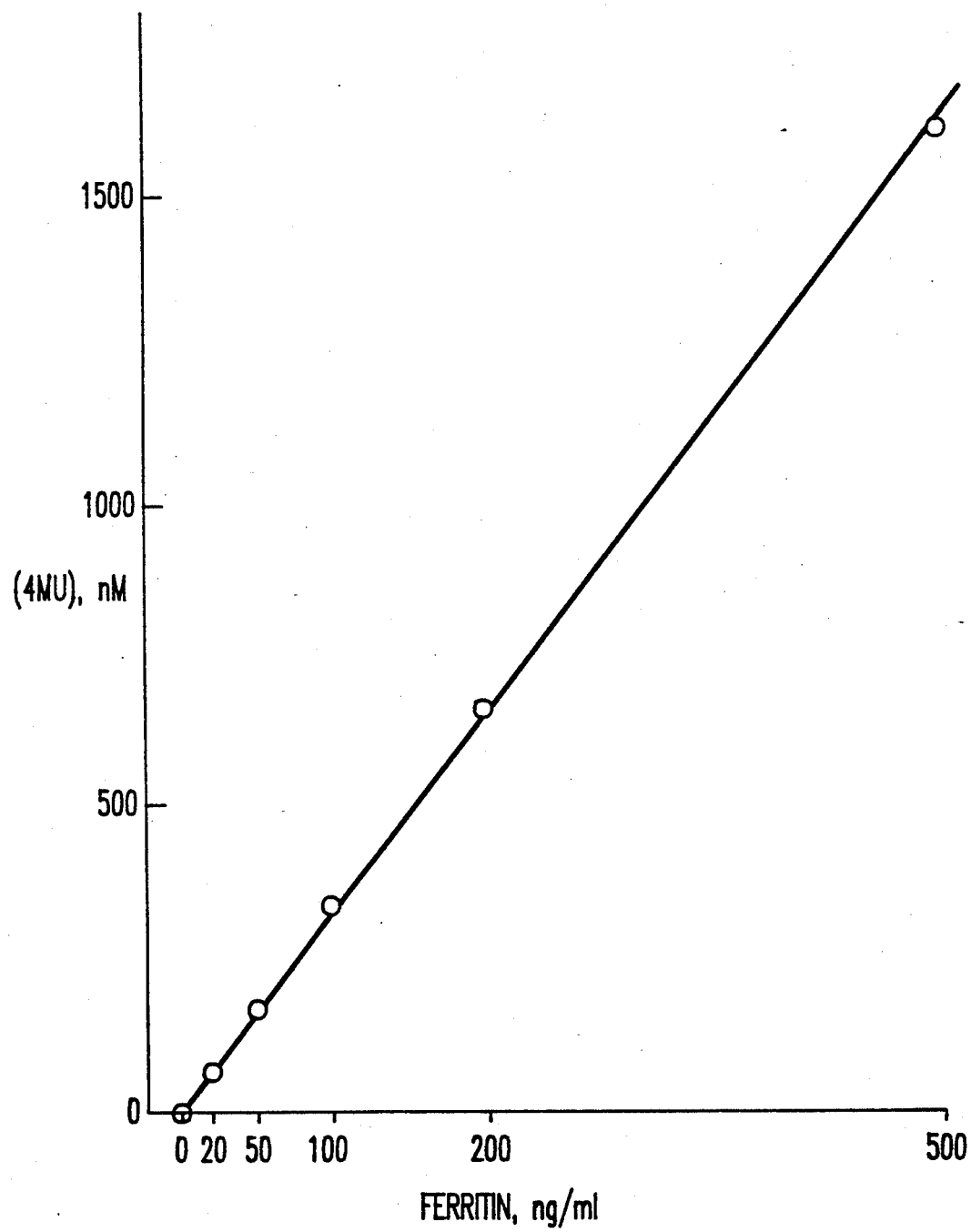
FIGS. 2 to 4 shows the results of the tests for detecting ferritin, α-fetoprotein (AFP) and human chorionic gonadotropin (HCG), respectively, in Example 10.
Figure 3:
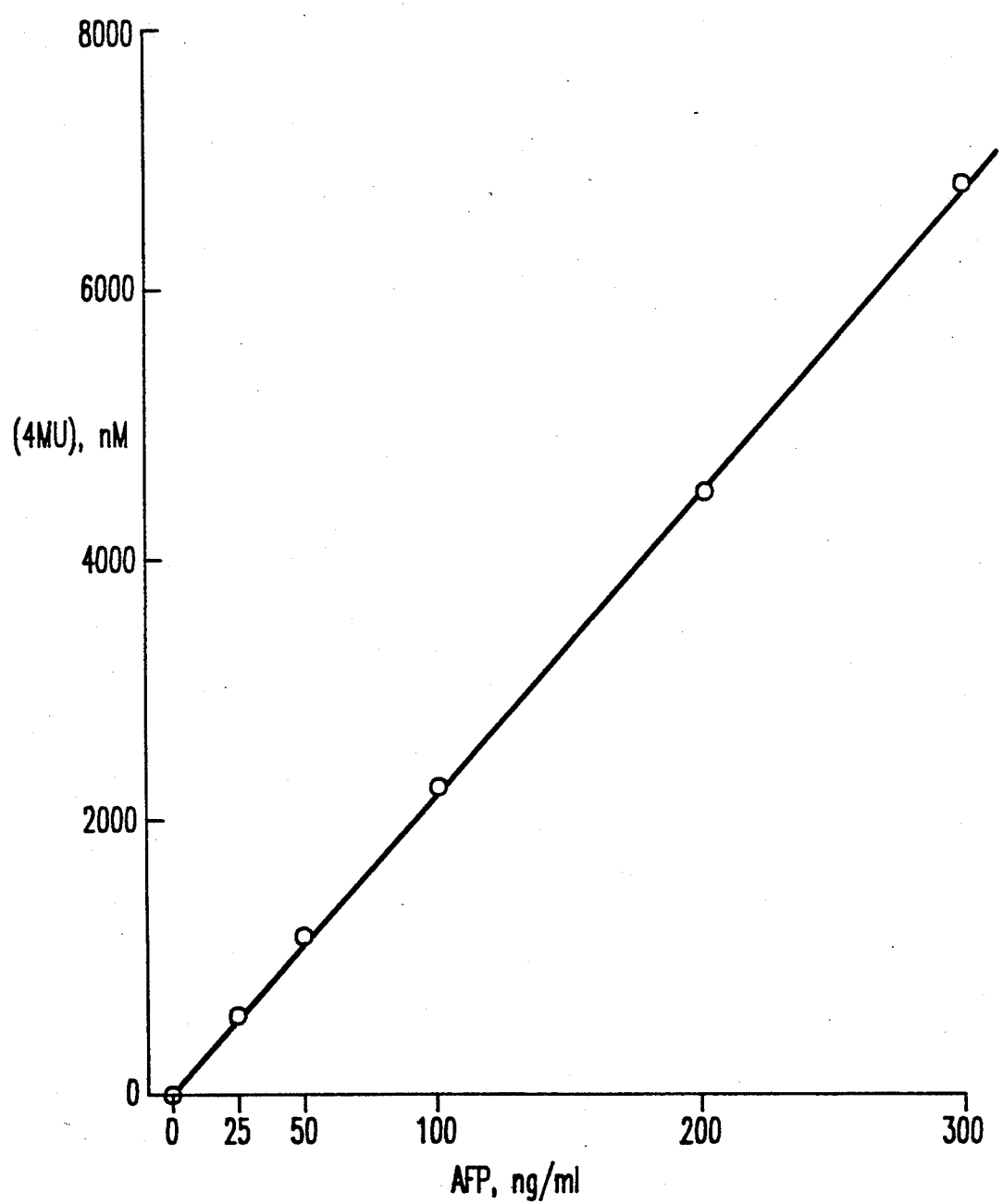
Figure 4:
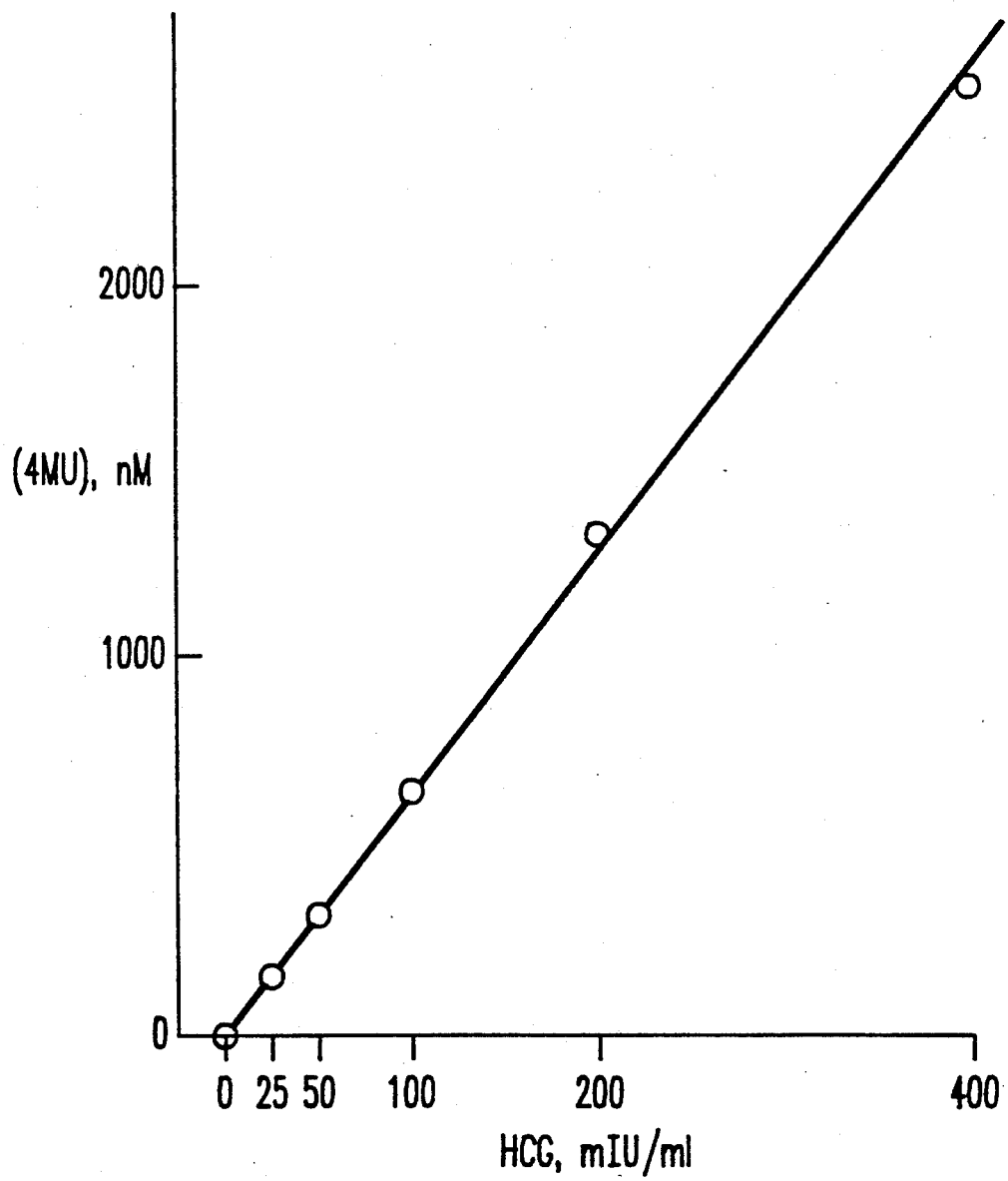

By using the polymer-coated magnetic resin beads (diameter: about 1.6 mm) obtained in Example 5(2) and having amino groups introduced to the surface by 1,6-diaminohexane, enzymatic immunoassays of ferritin, AFP (α-fetoprotein) and HCG (human chorionic gonadotropin) were conducted by a sandwich method. For each assay, 2,000 magnetic resin beads obtained in Example 5(2) were subjected to glutaraldehyde treatment and immobilization of antibodies in the same manner as in Example 8. Likewise, alkaline phosphatase-labelled antibodies were prepared in the same manner, and used for the sandwich method for immunoassays. Serums containing the respective antibodies and their amounts of use were as follows. Ferritin: 0, 20, 50, 100, 200, 500 ng/ml (amount used: 200 microliters each); AFP: 0, 25, 50, 100, 200, 300 ng/ml (amount used: 25 microliters each); HCG: 0, 25, 50, 100, 200, 400 mIU/ml (amount used: 50 microliters each). The number of the magnetic resin beads and the amounts of the enzyme-labelled antibody solutions used, were as follows. Ferritin: 12 beads, 125 microliters; AFP: 12 beads, 100 microliters; HCG: 12 beads, 100 microliters, for each assay. The antigen-antibody reaction was conducted at 37° C. for 40 minutes, and the enzyme-substrate reaction was conducted at 37° C. for 10 minutes. These reactions were conducted in the same manner as in Example 8. The results are shown in FIGS. 2 to 4. It is evident from each of these Figures that with respect to each of firritin, AFP and HCG, a good linear relationship is obtained within the range of measurement, and that non-specific adsorption at a 0 concentration is minimum. In the case of firritin, the substantially the same linearity and fluorescence intensity at the respective concentrations as in Example 8 were obtained, thus indicating that the magnetic resin beads obtained in Example 5(2) are substantially the same as those obtained in Example 5(3) in their performance.

EXAMPLE 11

By using the magnetic resin beads (diameter: about 1.6 mm) obtained by saponification in Examples 5(1) and 5(3), enzymatic immunoassays of L-thyroxine (T$_4$) were conducted by a competition method.

Figure 5:
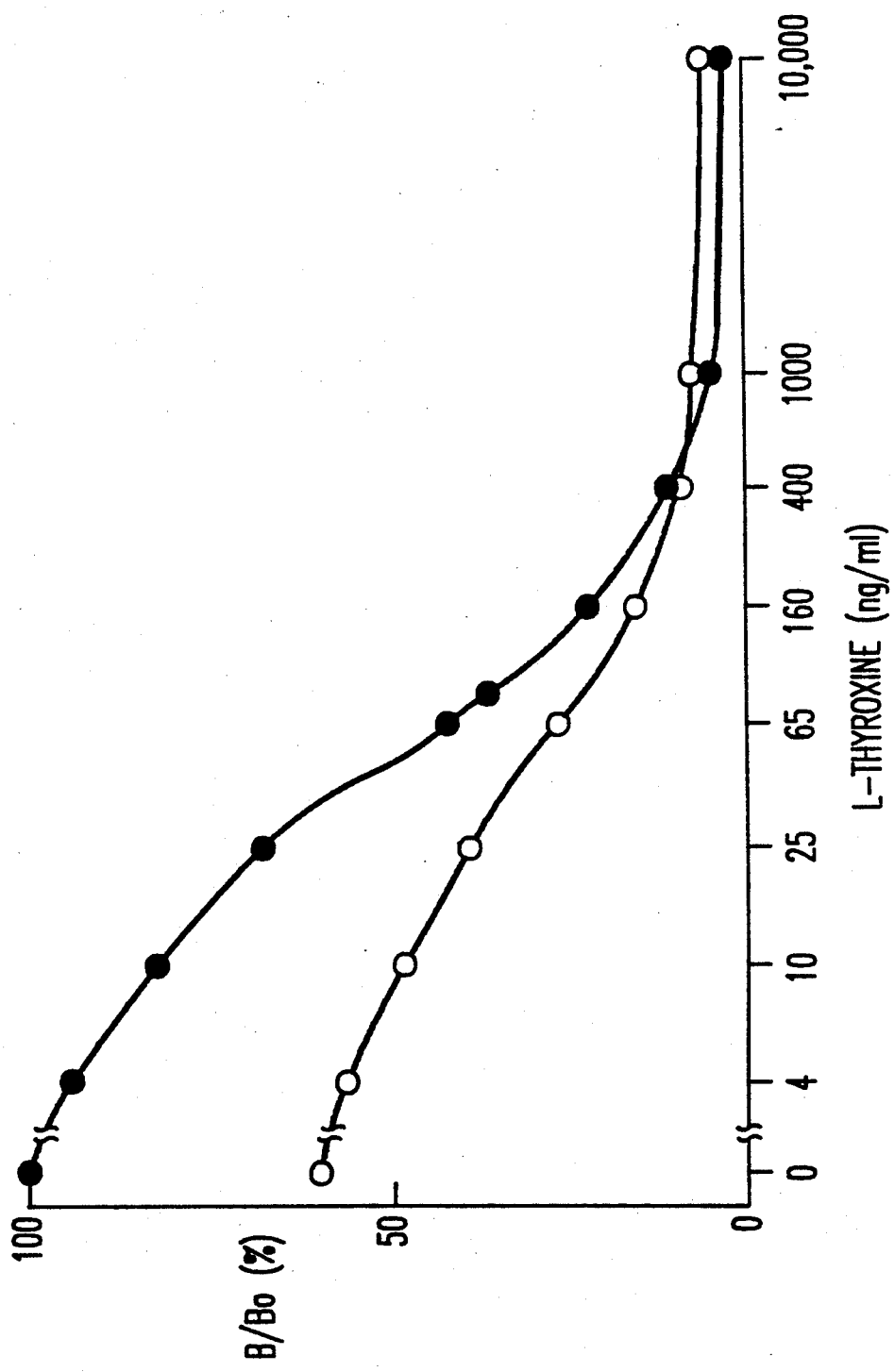
FIG. 5 is a graph showing the standard curve of L-thyroxine ($T_4$) in a competition method in Example 11.

The magnetic resin beads obtained in Example 5(1) already had many aldehyde groups on their surface, and anti-T$_4$ monoclonal antibodies were immobilized by utilizing these aldehyde groups in the same manner as described in Example 8 (acrolein method). Likewise, the beads obtained in Example 5(3) already had many primary alcoholic hydroxyl groups on their surface, and the immobilization of antibodies was conducted by N,N'-carbonyldiimidazole (CDI) method in the same manner as described in Example 8. Here, 200 μg of the anti-T$_4$ monoclonal antibodies were used for 2,000 magnetic resin beads. Then, in accordance with a known method, T$_4$ was chemically bonded to an alkaline phosphatase to obtain enzyme-labelled antigens. In each immunoassay, eight antibody-bound magnetic resin beads, 130 microliters of the enzyme-labelled antigen solution and 20 microliters of a serum containing a various concentration of T$_4$ (T$_4$ concentration: 0, 4, 10, 25, 65, 75, 160, 400, 1,000 and 10,000 ng/ml) were subjected to the antigen-antibody reaction and the enzyme-substrate reaction in the same manners as in Example 8, and the fluorescence intensity was measured. The results are shown in FIG. 5. In this Figure, the fluorescence intensity at various concentrations is represented by relative values based on the fluorescence intensity measured at a concentration of T$_4$ of 0 ng/ml by using the magnetic resin beads obtained by CDI method, being set at 100. In this Figure, ●:

CDI method; and
○: acrolein method.

It is evident from FIG. 5 that when the antibody-immobilized magnetic resin beads obtained by CDI method are employed, a good competition reaction curve is obtained. Further, it is evident that a non-specific adsorption to the antibody-immobilized magnetic resin beads is minimum according to this method. Whereas, those obtained by the acrolein method are not so good as those obtained by the CDI method in the reactivity, and certain non-specific adsorption is observed. However, these beads are still adequately useful for the immunoassays.

We claim:

1. A carrier for a biologically active component for immunoassay or enzymatic reaction, which comprises:
   a) a thermoplastic resin bead having an average diameter of from 0.05 to 20 mm,
   b) from 1 to 25% by weight, based on the bead, of a magnetically responsive powder having an average particle size of from 0.01 to 10 μm bound on the bead, and
   c) a polymer coated thereon in a thickness of from 2 to 30 μm, said polymer having a number average degree of polymerization of from 20 to 5000 and having or capable of having functional groups capable of binding the biologically active component.

2. The carrier according to claim 1, wherein the functional groups of the polymer (c) are selected from the group consisting of

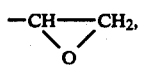

—CHO, —OH and —NH₂.

3. The carrier according to claim 1, wherein the bead is made of a thermoplastic resin selected from the group consisting of a polyolefin resin, a vinyl resin, a polyester resin, a polyamide resin, and a mixture thereof.

4. The carrier according to claim 1, wherein the bead is substantially spherical.

5. The carrier according to claim 1, wherein the magnetically responsive powder has an average particle size of from 0.01 to 10 μm and is made of iron, tri-iron tetroxide, nickel, iron-cobalt, silicon steel or a soft ferrite of the formula MFe₂O₄ wherein M is Mn, Zn, Ni, Cd, Cu, Mg, Sr or Ba.

6. The carrier according to claim 1, wherein the polymer (c) is a polymer of a monomer having the formula RCH=CR'—CHO wherein each of R and R' is a hydrogen atom, an alkyl group, a halogen-substituted alkyl group or a phenyl group, and having a total of from 3 to 10 carbon atoms.

7. The carrier according to claim 1, wherein the polymer (c) is a polymer having a repeating unit of the formula:

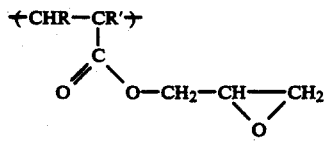

wherein each of R and R' is a hydrogen atom, an alkyl group, a halogen-substituted alkyl group or a phenyl group, and obtained from a monomer having a total of from 6 to 12 carbon atoms.

8. The carrier according to claim 1, wherein the polymer (c) is a polymer having —OH groups obtained by hydrolyzing a polymer having a repeating unit of the formula:

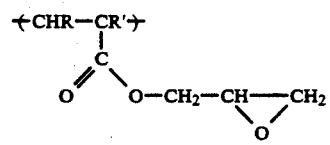

wherein each of R and R' is a hydrogen atom, an alkyl group, a halogen-substituted alkyl group or a phenyl group, and obtained from a monomer having a total of from 6 to 12 carbon atoms.

9. The carrier according to claim 1, wherein the polymer (c) is a polymer having —NH₂ groups obtained by aminating a polymer having a repeating unit of the formula:

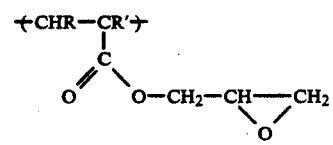

wherein each of R and R' is a hydrogen atom, an alkyl group, a halogen-substituted alkyl group or a phenyl group, and obtained from a monomer having a total of from 6 to 12 carbon atoms, with a diamine having the formula NH₂—R"—NH₂ wherein R" is an alkyl group, a halogen-substituted alkyl group or a phenyl group having a total of from 2 to 12 carbon atoms.

10. The carrier according to claim 1, wherein the polymer (c) is polyglycidyl methacrylate, a glycidyl methacrylate-tetraethyleneglycol dimethacrylate copolymer, an acrolein-tetraethyleneglycol dimethacrylate copolymer, polystyrene or polyvinyl chloride.

11. The carrier according to claim 1, wherein the functional groups of the polymer (c) are —OH groups activated by treatment with carbodiimidazole or —NH₂ groups activated by treatment with glutaraldehyde.

12. The carrier according to claim 1, wherein a biologically active component selected from the group consisting of antigens, antibodies and enzymes, is bound to the polymer (c).

13. A process for preparing the carrier defined by claim 1, which comprises depositing a magnetically responsive powder on the surface of the thermoplastic resin bead in an amount of from 1 to 25% by weight, based on the bead, and forming a layer of the polymer (c) on the bead in a thickness of from 2 to 30 μm.

14. The process according to claim 13, wherein the layer of the polymer (c) is formed by polymerizing a monomer having functional groups selected from the group consisting of

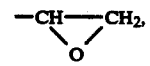

—CHO or —OH to form a polymer having the corresponding functional groups.

15. The process according to claim 14, wherein the polymer having

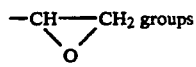

is hydrolyzed to convert the groups to —OH groups or treated with a diamine to introduce —NH$_2$ groups.

16. The process according to claim 14, wherein the polymer having —OH groups is treated with N,N'-carbonyldiimidazole for activation.

17. The process according to claim 14, wherein the polymer having

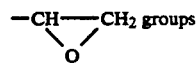

is partially hydrolyzed and reacted with a silane coupling agent having —NH$_2$ groups.

18. The process according to claim 15, wherein the polymer having —NH$_2$ groups is treated with glutaraldehyde for activation.

19. The process according to claim 13, wherein the thermoplastic bead is substantially spherical and is prepared by dispersing particles of a thermoplastic resin having a substantially uniform shape in a medium in which the resin is insoluble, at a temperature lower than the melting point of the resin and then heating the dispersion at a temperature of from the melting point of the resin to a temperature not higher than 30° C. above the melting point.

20. The process according to claim 13, which includes an additional step of treating the carrier with the biologically active component.

21. The carrier according to claim 1, wherein the bead is made of a thermoplastic resin wherein said thermoplastic resin is a copolymer resin.

* * * * *